United States Patent [19]
Pinchuk et al.

[11] Patent Number: 5,804,318
[45] Date of Patent: Sep. 8, 1998

[54] LUBRICIOUS HYDROGEL SURFACE MODIFICATION

[75] Inventors: Leonard Pinchuk, Miami; Yasushi P. Kato, Pembroke Pines, both of Fla.

[73] Assignee: Corvita Corporation, Miami, Fla.

[21] Appl. No.: 548,827

[22] Filed: Oct. 26, 1995

[51] Int. Cl.⁶ .......................... B32B 15/08; B32B 27/08; B32B 27/30; B05D 5/08

[52] U.S. Cl. ................... 428/421; 428/424.4; 428/447; 428/451; 428/463; 428/476.3; 428/483; 428/520; 428/522; 427/2.24; 427/2.25; 427/2.3; 427/2.31; 427/333; 427/337; 427/407.1; 623/1; 623/2; 623/3; 623/11; 623/901

[58] Field of Search .................. 427/299, 322, 427/301, 333, 337, 393.5, 407.1, 414, 2.24, 2.25, 2.3, 2.31; 525/303.1, 306, 307.1, 307.2, 307.4, 307.7; 623/11, 12, 1, 2, 3, 4, 5, 901; 428/36, 421, 424.4, 447, 451, 463, 476.3, 483, 520, 522

[56] References Cited

U.S. PATENT DOCUMENTS

| | | | |
|---|---|---|---|
| 3,639,141 | 2/1972 | Dyck | 117/47 A |
| 3,708,324 | 1/1973 | Stebleton | 117/47 R |
| 3,844,989 | 10/1974 | Harumiya et al. | 260/17.4 R |
| 3,846,353 | 11/1974 | Grotta | 260/9 |
| 4,521,564 | 6/1985 | Solomon et al. | 525/54.1 |
| 4,588,624 | 5/1986 | Nygren et al. | 428/36 |
| 4,737,544 | 4/1988 | McCain et al. | 525/54.1 |
| 4,820,302 | 4/1989 | Woodroof | 604/265 |
| 5,053,048 | 10/1991 | Pinchuk | 623/1 |
| 5,132,108 | 7/1992 | Narayanan et al. | 424/78.17 |
| 5,229,172 | 7/1993 | Cahalan et al. | 427/536 |
| 5,344,455 | 9/1994 | Keogh et al. | 623/11 |
| 5,422,405 | 6/1995 | Dairoku et al. | 525/384 |
| 5,563,056 | 10/1996 | Swan et al. | 435/180 |
| 5,607,475 | 3/1997 | Cahalan et al. | 623/11 |

OTHER PUBLICATIONS

"A New Non–Thrombogenic Surface Prepared by Selective Covalent Binding of Heparin Via a Modified Reducing Terminal Residue", *Biomat., Med. Dev., Art. Org.*, 11(2&3), pp. 161–173, (1983).

*Primary Examiner*—Vivian Chen
*Attorney, Agent, or Firm*—Lockwood, Alex, Fitzgibbon & Cummings

[57] ABSTRACT

New and improved lubrifying coatings for reducing the coefficients of friction of surfaces on medical devices include hydrophilic copolymers derived monoethylenically-unsaturated monomers including some monomers having pendant primary amine functionality and some monomers having pendant tertiary amine functionality. The lubricious hydrogel coatings are covalently bondable to epoxy functionalized surfaces on the medical equipment to provide firmly adherent hydrogel coatings that are slippery when wet. Epoxy functionalized surfaces are provided by epoxy functional or epoxy group containing silane coupling agents. The pendant tertiary amine moieties are readily convertible at alkaline pH to quaternary ammonium cations to which anionic anti-thrombogenic agents may be bonded. Three dimensional copolymer matrices may also be provided as coatings on the surfaces by crosslinking the copolymers before or after attachment to the surface being treated.

21 Claims, 4 Drawing Sheets

(FORMULA IV)

ACRYLAMIDE

2-DIMETHYLAMINOETHYL METHACRYLATE

N-(3-AMINOPROPYL)METHACYLAMIDE

LINEAR HYDROGEL

LINEAR HYDROGEL 1,2-GLYCIDYLPROPYL TRIMETHOXYSILANE
PRIMED SURFACE (FORMULA IV)

LINEAR HYDROGEL

GLUTERALDEHYDE OR FORMALDEHYDE
+ HEPARIN (FORMULA V)

LUBRICIOUS HYDROGEL SURFACE MODIFICATION

BACKGROUND OF THE INVENTION

The present invention generally relates to surface treatments and coatings intended to make the surfaces of objects more lubricious. More particularly, it relates to a new and improved bonded hydrogel coating treatment effective to significantly reduce the coefficient of friction of a surface and also provide non-thrombogenic coatings, if desired.

Natural and synthetic elastomers and polymers, especially silicone rubbers, are used for many medical applications because they are rather inert materials exhibiting good biocompatibility. Silicone rubbers and other natural and synthetic rubber materials suffer from poor surface lubricity, rendering their use in many medical and surgical applications undesirably problematic.

For example, pacemaker lead insulators made from silicone rubber do not easily slide past one another within the venous system, dramatically limiting their use in dual pacing applications. Hemostasis valves generally require the addition of silicone oils to enable catheters to slide through the valve opening. Many other medical devices such as penile implants suffer from poor lubricity when silicone tubes are inflated within silicone restraints. Poor contact surface lubricity causes sticking and/or hampered or unpredictable sliding performance, which may occur at inopportune times, such as during insertion of catheters. Poor slip characteristics between the catheter and the slide site may result in abrasion or erosion of the coating and stripped coating particles may contaminate the slide site. The surfaces of latex gloves are another example of a rubbery surface which must be powdered to facilitate or modify the surface friction properties to make it easier to slide the gloves on for use. The powder on the gloves gets everywhere and especially on surgical instruments which is undesirable.

Many prior chemistries and methods have been developed to render silicones and other rubbers more slippery, such as, for example, by the application of hydrophilic coatings, ion beam etching, and lubrication with silicone oils, to name but a few. The need for slippery surfaces for use in medical and other applications exists not only for rubbery or elastomeric substrates and devices but also for other polymeric and metallic shaped objects and devices. Further development of useful coatings is needed.

In order to overcome the shortcomings of the prior art methods and coatings, it is an object of the present invention to provide a new and improved slippery and lubricious coating or surface treatment for reducing the coefficient of friction of a surface of a medical device such as a catheter to facilitate movement and maneuverability of the device through a tortuous path such as in the vascular system.

It is another object of the present invention to provide a lubricious surface coating having an aqueous solvent base to promote ease of handling and reduce solvent pollutants and to minimize solvent damage to the underlying device surface.

It is a further object of the present invention to provide a new and improved coating for articles which is slippery when wet and may easily be ionically coupled with anticoagulant agents.

It is still another object of the present invention to provide a new and improved non-thrombogenic surface for medical devices.

SUMMARY OF THE INVENTION

In accordance with these and other objects, the present invention provides a new and improved lubricious surface modification or coating for reducing the coefficient of friction of a surface of a shaped article. The surface modification or coating comprises a covalently bound hydrophilic polymer matrix coating. More particularly, the slippery and non-thrombogenic surface comprises a hydrogel containing pendant primary and tertiary amine groups. At least some of the pendant tertiary amine groups are quaternized by adjusting the pH to the alkaline range. The anticoagulant agents, usually having a negative ionic charge, are ionically bound to the quaternary ammonium cations present in the hydrogel. The pendant primary amine groups on the hydrogel are used to covalently bind the hydrogel to the medical device surface which preferably has been epoxy-functionalized with an epoxy group functional silane priming/coupling agent. The bound gel can further be crosslinked by reacting with a crosslinker selected from divalent and polyvalent crosslinkers.

More particularly, in accordance with the present invention, a new and improved lubricious hydrogel coating bondable to an epoxy-functionalized surface portion of a medical device is provided, said coating comprising: a substantially linear, hydrophilic, vinyl addition copolymer including the following units:

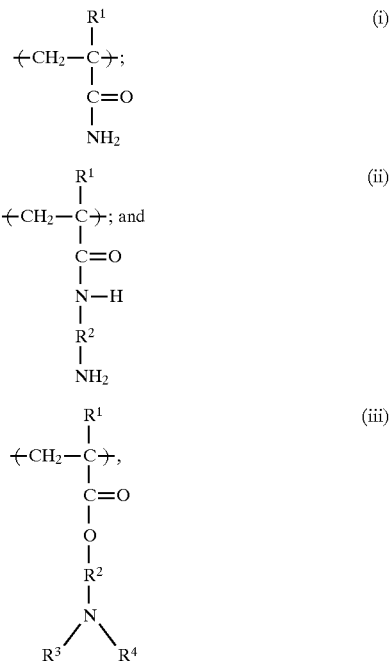

wherein $R^1$ is an H or $C_1$–$C_4$ alkyl group, $R^2$ is a divalent aliphatic, cycloaliphatic, aromatic or alkylaromatic group, and $R^3$ and $R^4$ are each independently selected from H or $C_1$–$C_4$ alkyl groups, said copolymer having a number average molecular weight of less than about 30,000.

In accordance with the preferred embodiment, the copolymer is formed and thereafter grafted onto the surface of the device via reaction between the pendant primary amine groups on the copolymer and epoxy groups bound to the surface of the device. The epoxy groups are provided in a trifunctional silane coupling agent which covalently bonds to hydroxyl groups present on the device surface. In the alternative, coupling agent may be pre-reacted with the copolymer and thereafter the resulting pendant trifunctional silane moieties now present on the copolymer may be reacted with the device surface. The anti-thrombogenic agents may be reacted with the pendant guaternized ammonium groups on the copolymer before or after grafting of the copolymer to the device surface. In addition, three dimensional matrices of crosslinked copolymers bound to and built up from the device surface with or without bound anionic anti-thrombogenic agents may also be provided. Other objects and advantages provided by the present invention will become apparent from the following Detailed Description and illustrative Examples.

DETAILED DESCRIPTION OF THE INVENTION

The surface modification or coating comprises a covalently bound hydrophilic polymer matrix coating. More particularly, the slippery and non-thrombogenic surface comprises a hydrogel containing pendant primary and tertiary amine groups. At least some of the pendant tertiary amine groups are quaternized by adjusting the pH to the alkaline range. The anticoagulant agents, usually having a negative ionic charge, are ionically bound to the quaternary ammonium cations present in the hydrogel. Protamine sulfate can also be used to further bind heparin wherein protamine sulfate is covalently bound to the hydrogel during the crosslinking procedure. The pendant primary amine groups on the hydrogel are used to covalently bind the hydrogel to the medical device surface which preferably contains an epoxy-functionalized active silane priming/coupling agent. The bound gel can further be crosslinked by reacting with bis-electrophiles, bis-alkylating agents, and bis-halides, such as $\alpha,\alpha'$-dichloro-p-xylene, bis-alkylbromide, formaldehyde, glutaraldehyde, aldehyde starch, glyoxal, diisocyanates, polyhydric aromatic groups with formaldehyde, and mixtures of any of the foregoing crosslinking agents.

The hydrogel backbone is composed predominantly of hydrophilic vinyl containing monomers such as acrylamide, 2-hydroxyethyl methacrylate, vinylpyrrolidone, vinylalcohol, acrylic acid, methacrylic acid and the like. By vinyl-containing monomers is meant any monomers otherwise suitable which contain mono-ethylenic unsaturation. The hydrogel backbone is of high purity, i.e., does not contain crosslinker contaminants and, when polymerized, is generally biocompatible in nature. The backbone may also optionally contain some minor amounts of hydrophobic co-monomers or groups, such as vinyl nitrile, butyl methacrylate and the like to enhance the physical properties of the resultant polymer.

Figure 1:
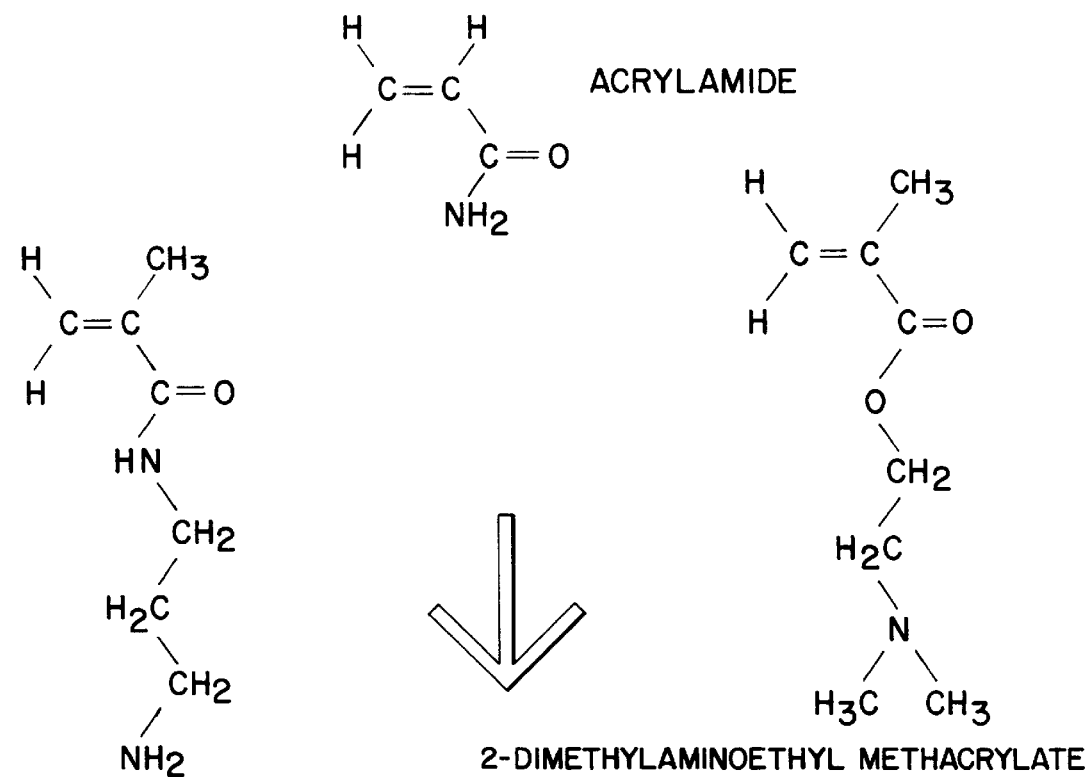
FIG. 1 presents chemical formulas to illustrate preparation of the preferred linear hydrogel copolymer in accordance with the invention.
Figure 1:
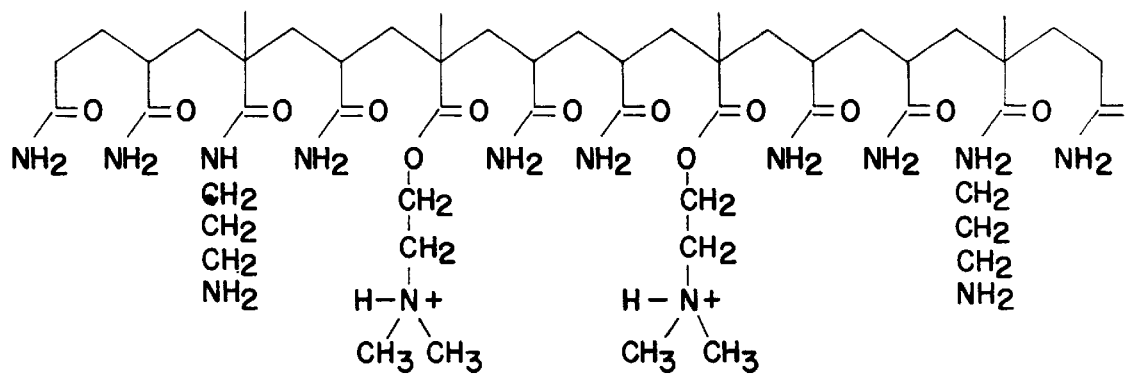

A preferred hydrogel in accordance with this invention includes acrylamide as the predominant backbone monomer. Added to the hydrogel backbone monomer comprising (i) units and prior to initiation of the polymerization reaction are small amounts (usually less than 10%) of comonomers containing primary and tertiary amines, the (ii) and (iii) units, respectively. An example of a primary amine containing comonomer for use as the (ii) units is N-(3-aminopropyl) methacrylamide. An example of a tertiary amine containing comonomer for use as the (iii) units is N,N-dimethyl-2-aminoethyl methacrylate. Each of these specific examples is shown in FIG. 1, and the preferred copolymer may be represented by the formula I shown in FIG. 1.

The three preferred comonomers, acrylamide, N-(3-aminopropyl) methacrylamide and N,N-dimethyl-2-aminoethyl methacrylate are reacted together by being added to a reaction mixture followed by the addition of a free radical initiator such as ammonium persulfate. The comonomers may be added in the form of their hydrochloride salts. Such vinyl-addition polymerization reactions are well known by those versed in polymer chemistry and can be promoted by the addition of coinitiators, heat, light, deinhibitors and the like. The reaction is typically performed in deaerated dilute aqueous solution, with or without heat. There are no bis-vinyl crosslinkers added to the reaction medium to form crosslinks. Formula I illustrates the linear water soluble hydrogel that is formed by this addition reaction. It is important to note that the copolymer thus formed is linear, water soluble and contains both primary and tertiary amines as pendant groups. The tertiary amines are quaternized in alkaline pH.

The medical device surface to be coated with the hydrogel is preferably comprised of polyurethane, nylon, polyamide, polyvinylchloride, polyolefin, metal or virtually any surface capable of being coupled to a silane priming agent or which contains groups reactive with the pendant primary amine groups. In addition, the medical device surface can take the form of a totally inert surface that has been activated by actinic radiation or plasma treated to provide accessible hydroxyl moieties. Furthermore, the hydrogel can be mechanically bound within a porous matrix by gelling or crosslinking the linear polymer in the interstices of the porous matrix.

Figure 2:
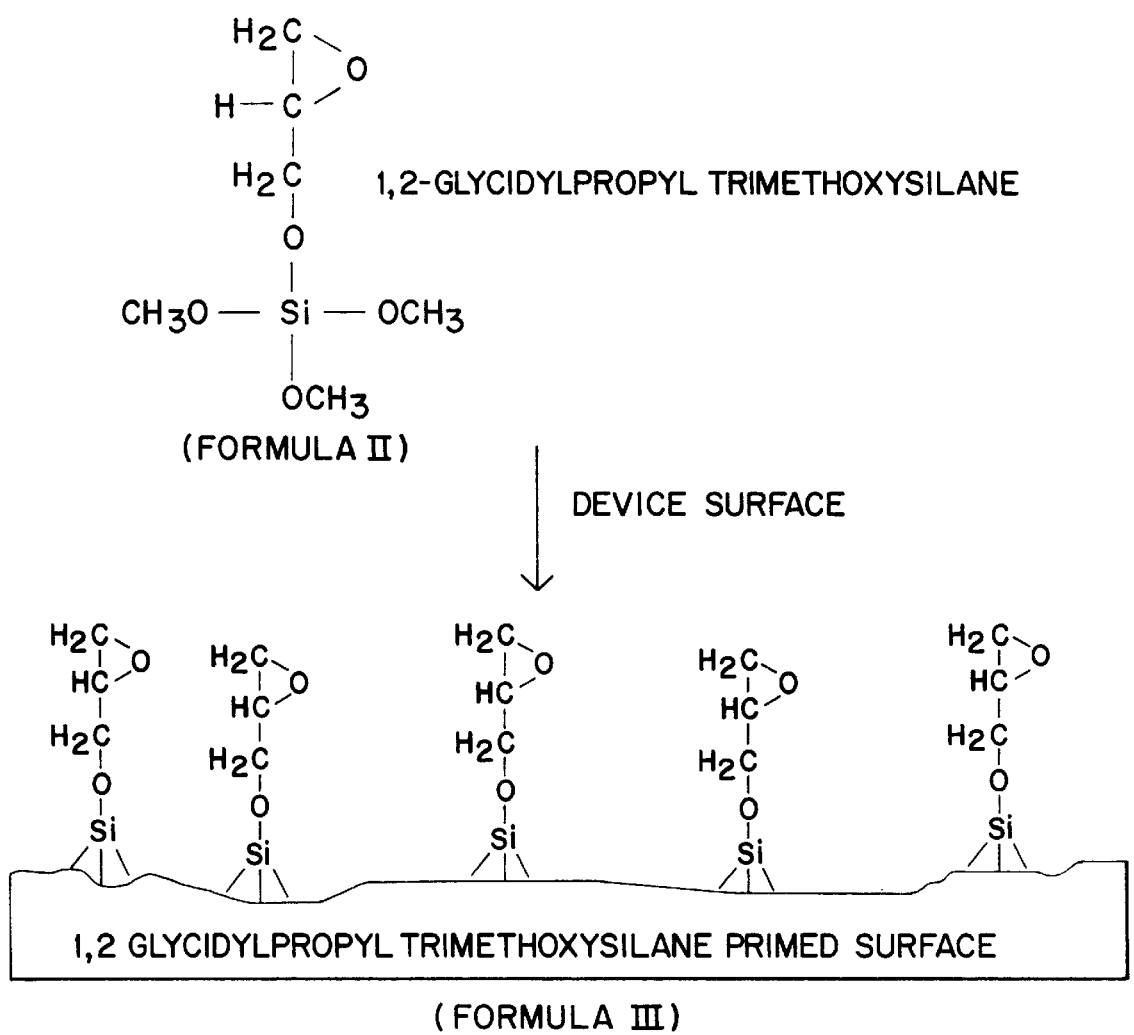
FIG. 2 presents chemical formulas to illustrate priming of the surface of a device.

If the hydrogel is to be covalently bound to the surface of a medical device, the preferred silane coupling agent is 1,2-glycidylpropyl trimethoxysilane, depicted in FIG. 2 as formula II.

Other silane agents that will function in this capacity include isocyanate containing silanes, epoxy containing silanes and amine containing silanes. The nature of the silane leaving group should include methoxy, ethoxy, acetoxy, halogens, hydrogen, hydroxyl and the like. In addition, bis-functional molecules, such as methylene diisocyanate (MDI), glutaraldehyde and the like, will also function in this capacity.

It is preferable that the silane coupling agent be soluble in aqueous or alcohol solvents to facilitate coating the medical device surface. 1,2-glycidylpropyltrimethoxysilane is preferred due to its solubility in both water, ethanol and combinations of the above. The epoxy (glycidyl) group is highly reactive to pendant primary amine groups preferentially over hydroxyl groups, thereby facilitating bonding to the pendant amine containing hydrogel.

The silane is activated by dissolving it in 95% ethanol and 5% water (approximately 2% solids). The water containing solution displaces the methoxy groups or other leaving groups on the silane and provides the trihydroxyl functionality. This trihydroxyl functionality is reacted to hydroxyl groups on the surface to be coated with concomitant release of water. In general, the medical device surface is dipped into this priming solution where the silane moiety of the coupling agent is reacted to the device surface. This reaction may be accelerated and actuated by performing this step at an elevated temperature (50° to 110° C.). The resultant primed surface is illustrated in FIG. 2 as formula III.

Figure 3:
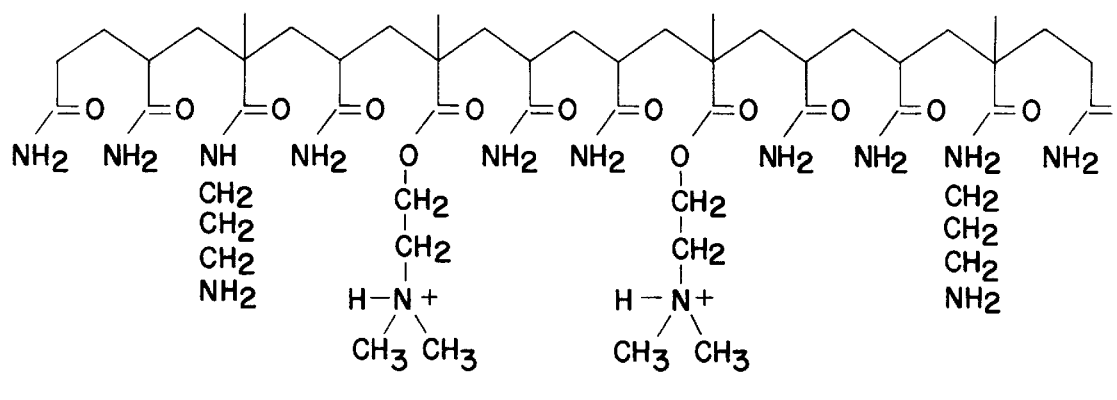
FIG. 3 represents chemical formulas to illustrate the covalently bound surface coating.
Figure 3:
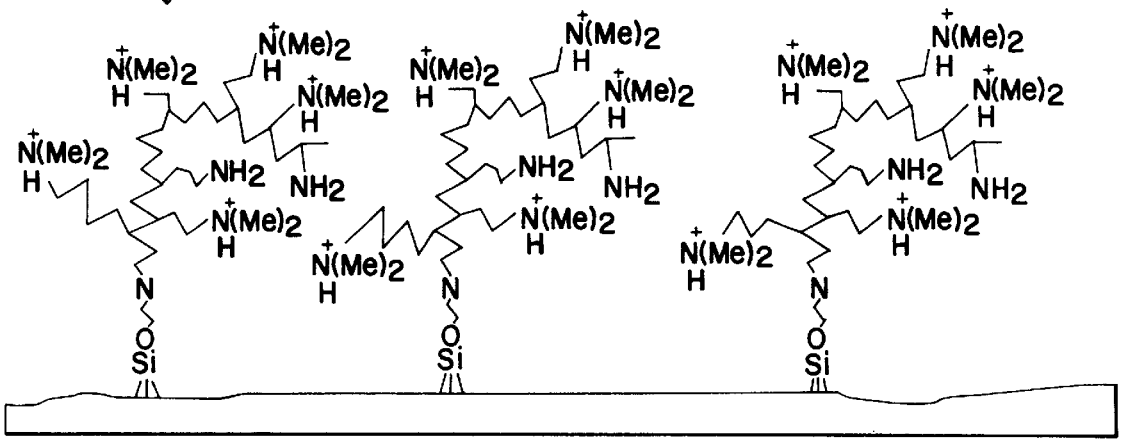

The primed surface is rinsed in ethanol to remove unreacted coupling agent and is then dipped into the hydrogel solution containing the copolymer depicted by formula I. The glycidyl or epoxy groups on the surface react with the pendant primary amine moieties on the hydrogel, to provide a covalently bound coating illustrated in FIG. 3 as formula IV.

The result is a surface coated and covalently bound to a hydrogel containing pendant tertiary amine groups. These tertiary amine groups may be converted to quaternary ammonium cationic groups by exposing the coated substrate or copolymer to alkaline pH. The hydrogel surface is now slippery or lubricious.

The quaternary ammonium cation-containing surface is then rendered non-thrombogenic by equilibrating the hydrogel in a solution of an anticoagulant, such as heparin sulfate. The bond between heparin and the hydrogel is ionic and the heparin slowly releases with time into the surrounding body fluids to prevent localized clotting. It can also be appreciated that heparin can be added to the hydrogel prior to bonding to the silane. In addition, the silane coupling agent can be bound to the hydrogel prior to bonding to the medical device surface. In accordance with this aspect of the invention, the copolymer may comprise at least some (iv) units having the formula:

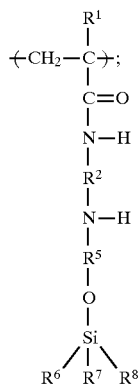

wherein $R^1$ is an H or $C_1$–$C_4$ alkyl group, $R^2$ and $R^5$ are each independently selected from a divalent aliphatic, cycloaliphatic, aromatic or alkylaromatic groups, and $R^6$, $R^7$ and $R^8$ are each independently selected from hydrogen, hydroxy, halogen, alkoxy, and acyloxy groups. The trifunctional silane moieties on the copolymer may be employed to anchor the copolymer coating to the device surface.

Figure 4:
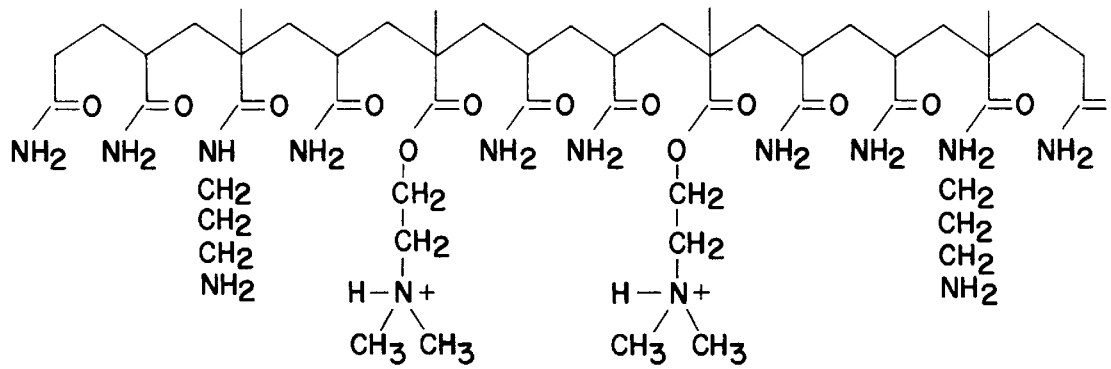
FIG. 4 presents chemical formulas to illustrate crosslinking of the linear hydrogel combined with anticoagulant loading.
Figure 4:
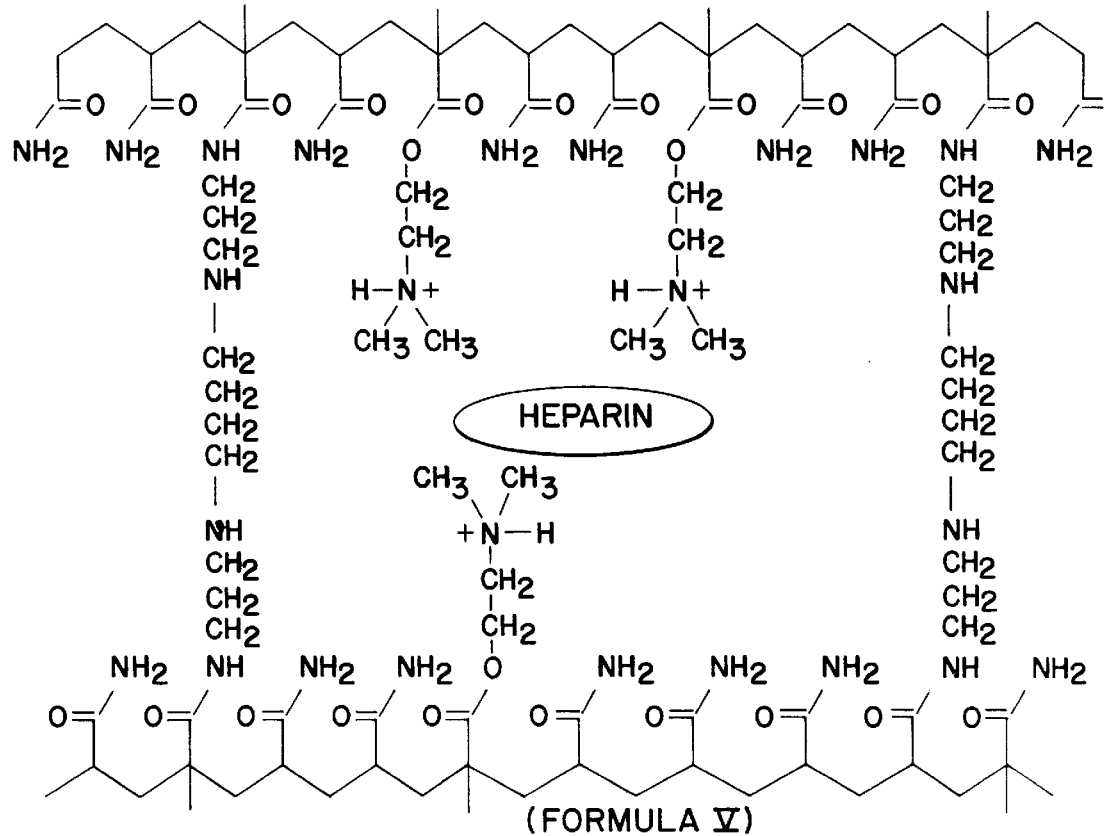

In accordance with the invention the linear hydrogel may be further reacted with a crosslinker, such as a dialdehyde, e.g., glutaraldehyde to crosslink the hydrogel. This step can be as illustrated in FIG. 4 to form a structure such as depicted by formula V in that figure. This crosslinker method may be used to obtain thick surfaces of hydrogel and more heparin loading. This procedure can also be used to crosslink or trap the gel in the interstices of a porous device such as a vascular graft. Protamine sulfate can also be diffused or mixed into the gel and crosslinked to the gel with the glutaraldehyde crosslinker. The gel can then be further complexed with anticoagulant.

If the surface is primed with a silane coupling agent containing primary amines, such as aminopropylaminoethyl triacetoxysilane, the aldehyde will couple the primary amines on the silane coupling agent to the primary amines on the gel to effectively produce a covalently bound thick gel.

DESCRIPTION OF THE PREFERRED EMBODIMENTS

Example 1

Approximately 1 mole of acrylamide (23.6 g) was mixed with 0.02 moles of N-3-aminopropyl methacrylamide (1.2 g) and 0.03 moles of 2-dimethylaminoethyl methacrylate (1.6 g). The above mixture was diluted in dearated water (200 mls) with 0.26 moles isopropyl alcohol (7 mls) and was polymerized by the addition of 0.15 g ammonium persulfate and heat at 65° C. for 3 hours. The thickened water soluble solution was included the linear hydrogel containing primary and tertiary amine groups of formula I.

Example 2

A polyurethane catheter was cleaned in ethanol and immersed in a solution of 93% ethanol, 5% water, and the silane coupling agent, 1,2-glycidylpropyl trimethoxysilane (2%) for approximately 5 minutes. The primed catheter was removed and rinsed in ethanol/water and immersed in the hydrogel solution of Example 1 for approximately 10 minutes. The catheter was then removed and heated to 70° C. to further react the amine groups to the epoxide groups (approximately 10 minutes). The coated catheter was rinsed in water and then immersed in a 2% heparin, 2% sodium bicarbonate solution for one hour. The catheter thus formed had a slippery heparin containing surface.

Example 3

To the hydrogel solution prepared in Example 1 was added 2% heparin sulfate. An epoxy-functionalized silane-primed catheter was dipped into this hydrogel/heparin solution, and the gel was permitted to bond to the catheter. The catheter thus formed had a slippery heparin containing surface.

Example 4

To the hydrogel solution of Example 1 was added 1,2-glycidylpropyl trimethoxysilane, and the hydrogel and primer mixture was heated for one hour at 70° C. A clean polyurethane catheter was dipped into this reaction media, and the gel was directly bound to the surface via the pendant silane groups.

Example 5

The hydrogel in Example 1, diluted to 6.5% solids, was vacuum impregnated into a porous vascular graft. The graft containing the soluble hydrogel was removed from the hydrogel solution and immediately dipped into a solution containing 10% formaldehyde (at alkaline pH) for 30 minutes. The gel was crosslinked in this manner. Heparin was then absorbed into the gel by equilibrating the graft in 2% heparin for four hours. The graft was rendered non-thrombogenic.

Example 6

The hydrogel in Example 1, diluted to 6.5% solids, was mixed with protamine sulfate, and the resulting mixture was vacuum impregnated into a porous vascular graft. The graft containing the soluble hydrogel was removed from the hydrogel solution and immediately dipped into a solution containing 10% formaldehyde (at alkaline pH) for 30 minutes. The hydrogel and protamine sulfate was crosslinked in this manner. Heparin was then absorbed into the gel by equilibrating the graft in 2% heparin for one hour. The graft was rendered non-thrombogenic by having the heparin then complexed to the gel and to bound protamine to provide a non-thrombogenic coating.

Example 7

A non-thrombogenic coated catheter was prepared in accordance with the methods of Examples 4 and 5, except that 1% glutaraldehyde was used instead of formaldehyde. The hydrogel is yellow in color as opposed to the clear gel prepared with formaldehyde.

Example 8

A nylon catheter was coated with the silane coupling agent 1,2-glycidylpropyltriacetoxysilane using the same solvent mixture as Example 2; i.e., 95% ethanol, 5% water, 2% primer. The silane-coated catheter containing epoxy groups was then cured at 70° C. for 10 minutes. The primed catheter was then dipped into the hydrogel solution of Example 1, then dried at 70° C. for 10 more minutes. The thus coated catheter contained a very thick layer (0.1 to 1 mm) of crosslinked hydrogel containing primary and tertiary amines. Heparin is absorbed into the gel by immersing the gel-containing catheter in 2% heparin in alkaline pH solution for one hour.

Example 9

The procedure of Example 8 was followed except that 2% protamine sulfate was mixed into the hydrogel prior to crosslinking. The protamine was crosslinked to the gel during the addition of formaldehyde. Heparin was coupled ionically to both the quaternized amines and the protamine on the gel.

Although the present invention has been described with reference to certain preferred embodiments, modifications or changes may be made therein by those skilled in this art. For example, instead of an acrylamide backbone being used, backbones formed of other hydrophilic vinyl-addition monomers might also be used such as acrylic acid or methacrylic acid. All such obvious modifications or changes may be made herein by those skilled in this art without departing from the scope and spirit of this invention as defined by the appended claims.

What is claimed is:

1. A shaped medical device containing at least one surface portion, said medical device comprising:

a shaped medical device containing a body having at least one surface portion;

a lubricious and adherent hydrophilic vinyl addition copolymer coating disposed on said surface portion, said copolymer coating including a hydrophilic vinyl addition copolymer containing pendant primary amine functionality and pendant tertiary amine functionality, said coating being covalently bonded via its pendant primary amine group to epoxy functionalized coupling agents bonded to said surface portion; and said lubricious and adherent coating is a linear, hydrophilic, vinyl addition copolymer containing the following units:

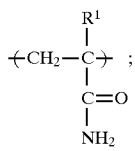
(i)

-continued

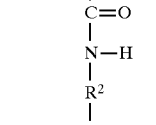
(ii)

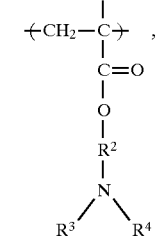
(iii)

wherein $R^1$ is an H or $C_1$–$C_4$ alkyl group, $R^2$ is a divalent aliphatic, cycloaliphatic, aromatic or alkylaromatic group, and $R^3$ and $R^4$ are each independently selected from H or $C_1$–$C_4$ alkyl groups, said copolymer having a number average molecular weight of less than about 30,000.

2. The medical device as defined in claim 1, wherein said copolymer contains from about 80% to about 99% by weight of said (i) units, from about 0.5% to about 10% by weight of said (ii) units; and from 0.5% to about 10% by weight of said (iii) units, based on the total weight of said copolymer.

3. The medical device as defined in claim 1, wherein, in said copolymer, said (i) units are derived from acrylamide monomeric units, said (ii) units are derived from N-3-aminopropyl methacrylamide monomeric units, and said (iii) units are derived from N,N-dimethyl-2-aminoethyl methacrylate monomeric units.

4. The medical device as defined in claim 1, wherein said copolymer is present in an aqueous solution at alkaline pH, such that at least some tertiary amine groups present in said (iii) units are converted to quaternary ammonium cations to which anionic anti-thrombogenic agents are ionically bonded to provide a non-thrombogenic coating.

5. The medical device as defined in claim 4, wherein said copolymer and ionically bonded anti-thrombogenic agent is cross-linked with a crosslinker selected from divalent and polyvalent crosslinking agents to provide a three dimensional, anti-thrombogenic and lubricious coating matrix bonded to said epoxy-functionalized surface portion.

6. The medical device as defined in claim 1, wherein said copolymer is cross-linked with a crosslinker selected from divalent and polyvalent cross-linking agents to provide a three dimensional lubricious coating matrix bonded to said epoxy-functionalized surface portion.

7. The medical device as defined in claim 1, wherein said medical device is selected from catheters, tubing, vascular graphs, cardiac pacemaker leads, heart diaphragm, heart valves, sutures, needles, angioplasty devices, prostheses, glass beakers, dialysis membranes, filters and sensors.

8. The medical device as defined in claim 1, wherein said surface portion comprises a surface material selected from polytetrafluoroethylenes, polyamides, polyesters, polyurethanes, polysiloxanes, polyolefins, and metals.

9. A shaped medical device containing at least one surface portion, said medical device comprising:

a shaped medical device containing a body having at least one surface portion;

a lubricious and adherent hydrophilic vinyl addition copolymer coating disposed on said surface portion, said copolymer coating including a hydrophilic vinyl addition copolymer containing pendant primary amine functionality and pendant tertiary amine functionality, said coating being covalently bonded via its pendant primary amine groups to a hydroxy-functionalized surface portion of said medical device; and said lubricious and adherent coating is a linear hydrophilic vinyl additional copolymer including the following units:

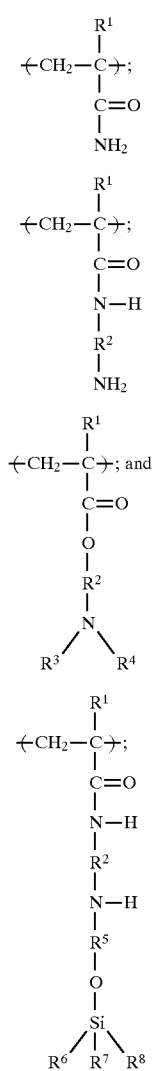

wherein $R^1$ is an H or $C_1$–$C_4$ alkyl group, $R^2$ and $R^5$ are each independently selected from a divalent aliphatic, cycloaliphatic, aromatic or alkylaromatic groups, $R^3$ and $R^4$ are each independently selected from H or $C_1$–$C_4$ alkyl groups, $R^6$, $R^7$ and $R^8$ are each independently selected from hydrogen, hydroxy, halogen, alkoxy, and acyloxy groups, said copolymer having a number average molecular weight of less than about 30,000.

10. The medical device as defined in claim 9, wherein said medical device is selected from catheters, tubing, vascular graphs, cardiac pacemaker leads, heart diaphragms, heart valves, sutures, needles, angioplasty devices, prostheses, glass beakers, dialysis membranes, filters and sensors.

11. The medical device as defined in claim 9, wherein said surface portion comprises a surface material selected from polytetrafluoroethylenes, polyamides, polyesters, polyurethanes, polysiloxanes, polyolefins, and metals.

12. The medical device as defined in claim 9, wherein, in said copolymer, said (i) units comprise from about 80% to about 99.0% by weight, said (iii) units comprise from about 0.5% to about 10% by weight and said (ii) and (iv) units combined comprise about 0.5% to about 10% by weight, based on the total weight of said copolymer.

13. The medical device as defined in claim 9, wherein said (i) units are acrylamide units, said (ii) units are N-3-aminopropyl-methacrylamide units, said (iii) units are N,N-dimethyl-2-aminoethyl methacrylate units, and said (iv) units are N-3-trimethoxysilyloxypropyl-3-aminopropyl methacrylamide units.

14. The medical device as defined in claim 9, wherein said copolymer is present in an aqueous solution at alkaline pH such that the (iii) units include quaternary ammonium cations to which anionic anti-thrombogenic agents are ionically bonded.

15. The medical device as defined in claim 9, wherein said copolymer is cross-linked with crosslinker selected from divalent and polyvalent cross-linking agents to provide a three dimensional lubricious coating matrix bonded to said hydroxy functional surface portion.

16. The medical device as defined in claim 15, wherein said anti-thrombogenic agent-bonded copolymer is cross-linked with a crosslinker selected from divalent and polyvalent crosslinking agents to provide a three dimensional anti-thrombogenic and lubricious coating matrix bonded to said hydroxy functional surface portion.

17. A method for making a lubricious bound coating on a medical device, said method comprising:

forming a reaction mixture including at least one hydrophilic vinyl addition polymerizable monomer having pendant primary amine functionality and at least one vinyl addition polymerizable monomer having pendant tertiary amine functionality, in an aqueous solution containing a vinyl addition polymerization catalyst;

heating the reaction mixture to commence polymerization of said monomers and permitting addition polymerization to proceed until formation of a solution containing a linear, hydrophilic vinyl addition copolymer including a vinyl addition backbone having randomly distributed units with pendant primary amine functionality and pendant tertiary amine functionality and having a number average molecular weight of less than about 30,000 is substantially complete; and contacting an epoxy-functionalized surface portion of a medical device to be coated with the copolymer solution to permit covalent bonding to proceed between pendant primary amine groups on the copolymer and epoxy groups present on the surface portion to covalently bond the hydrophilic copolymer coating to said surface portion.

18. The method as defined in claim 17, further comprising the step of providing an epoxy-functionalized surface portion on said medical device by:

providing a medical device with a surface portion to be treated and coated; and contacting said surface portion with an epoxy-functional silane coupling agent and reacting silane moieties on said coupling agent with hydroxyl groups present on the surface portion of said device to provide an epoxy functionalized surface portion.

19. The method as defined in claim 17, further comprising the step of contacting the copolymer with an alkaline pH solution to quaternize at least some of said pendant tertiary amine groups to form pendant quaternary ammonium cations on said copolymer; and thereafter ionically bonding at least one anionic anti-thrombogenic agent to said pendant cationic group by contacting the quaternized copolymer with a solution of said anionic anti-thrombogenic agent until ionic bonding is substantially complete.

20. The method as defined in claim 17, further comprising the step of adding a crosslinker to the reaction mixture before polymerization and before grafting onto the surface portion to provide a three-dimensional crosslinked copolymer matrix covalently bonded to said surface portion.

21. The method as defined in claim 17, wherein said anti-thrombogenic agent is heparin sulfate.

\* \* \* \* \*